United States Patent [19]

Ogino et al.

[11] Patent Number: 5,392,780
[45] Date of Patent: Feb. 28, 1995

[54] APPARATUS FOR MEASURING BIOLOGICAL SIGNAL

[75] Inventors: Yoshio Ogino; Kideki Ito, both of Tokyo, Japan

[73] Assignee: Nihon Kogden Corporation, Tokyo, Japan

[21] Appl. No.: 991,754

[22] Filed: Dec. 17, 1992

[30] Foreign Application Priority Data

Dec. 19, 1991 [JP] Japan .................... 3-336639

[51] Int. Cl.$^6$ ............................................. A61B 5/02
[52] U.S. Cl. ................................................ 128/670
[58] Field of Search ............... 128/670, 671, 696, 700, 128/710, 709, 712; 364/413.02, 413.03, 413.06, 413.22; 346/33 ME

[56] References Cited

U.S. PATENT DOCUMENTS

| | | | |
|---|---|---|---|
| 3,548,813 | 12/1970 | Berner | 364/413.06 |
| 4,757,824 | 7/1988 | Chaumet | 128/700 X |
| 4,887,607 | 12/1989 | Beatty | 128/670 |
| 4,960,129 | 10/1990 | de Paola et al. | 128/700 X |
| 4,964,410 | 10/1990 | Leahey et al. | 128/710 X |

*Primary Examiner*—Lee S. Cohen
*Assistant Examiner*—Samuel Gilbert
*Attorney, Agent, or Firm*—Sughrue, Mion, Zinn, Macpeak & Seas

[57] ABSTRACT

An object of the present invention is to provide an apparatus for measuring biological signals, which is capable of displaying marker lines on a time axis in synchronism with a particular position of a reference wave so that, if an electrocardiogram is selected as the reference wave, a plurality of other biological signals can be monitored in comparison with the electrocardiogram. According to the present invention, an apparatus for measuring biological signals includes an input unit for simultaneously receiving and amplifying a plurality of biological signal waveforms; a memory device for storing the plurality of biological signal waveforms input through the input device; a marker line synchronizing position setting device for determining a marker position by setting an arbitrary position of at least a single biological signal waveform that serves as a reference signal selected from the plurality of biological signal waveforms stored in the memory device; a marker line generating device for generating a marker line at the position set by the marker line synchronizing position setting device; and a display device for displaying the plurality of biological signal waveforms stored in the memory device and displaying the marker line generated by the marker line generating device such that it intersects the time axis of the plurality of biological signal waveforms orthogonally.

23 Claims, 5 Drawing Sheets

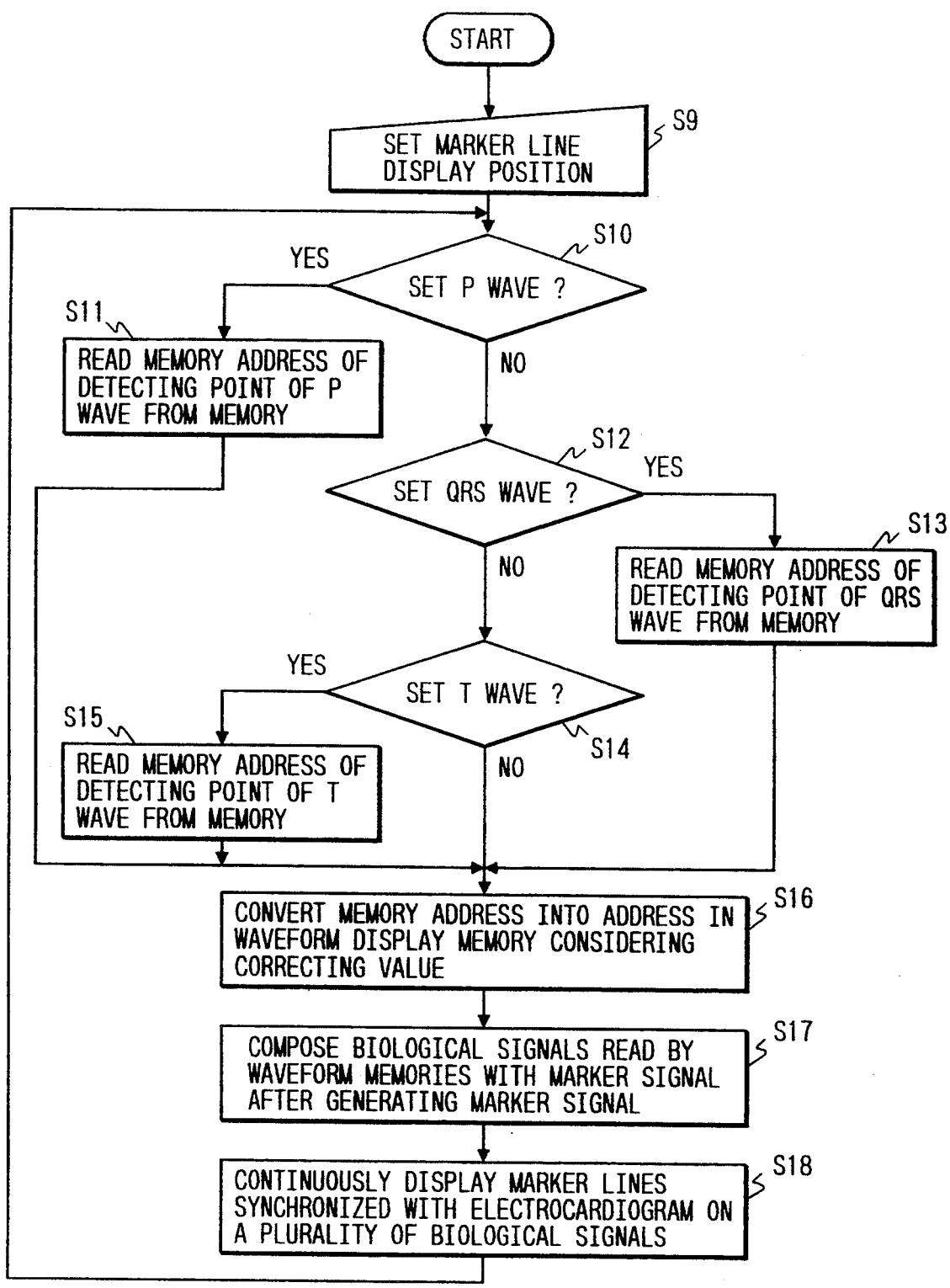

APPARATUS FOR MEASURING BIOLOGICAL SIGNAL

BACKGROUND OF THE INVENTION

The invention relates to an apparatus for measuring biological signals, which is capable of displaying marker lines on a time axis in synchronism with a particular position of a reference wave so that, if an electrocardiogram is selected as the reference wave, a plurality of other biological signals can be monitored in comparison with the electrocardiogram.

A polygraph, which is a multichannel monitoring apparatus, can monitor a plurality of biological signals such as an electrocardiogram, a pulse wave, a phonocardiogram, and blood pressure waves measured during a cardiac catheter examination while displaying them simultaneously on the screen of a monitor or can record the plurality of biological signals simultaneously by a printer.

When biological signals to be monitored are circulatory ones, a plurality of biological signals are generated simultaneously in synchronism with a cardiac cycle. It is for this reason that the waveforms of the biological signals displayed on the monitor screen or recorded on the recording sheet simultaneously are studied in phase with the cardiac cycle. In this case, a biological signal whose cardiac cycle is distinct is picked up as a reference for comparison among biological signals.

For example, in the case of a phonocardiogram that is an acoustic waveform generated as a result of the mechanical activity of a heart, it is difficult to distinguish only by the phonocardiogram a sound I generated as a result of a close of atrioventricular valves from a sound II generated as a result of a close of semilunar valves. Thus, the operation of distinguishing the sound I from the sound II with reference to an electrocardiogram is involved.

In the case of a blood pressure wave measured during a cardiac catheter examination, the waveform and amplitude thereof vary greatly depending on the position at which a catheter is inserted. As a result, it is difficult to locate the part of the heart from which the waveform is obtained only by the blood pressure wave. Thus, an electrocardiogram is referred to, again, in order to study the blood pressure wave.

Electrocardiograms and pulse waves are often used as reference waveforms for other biological signals since their cardiac cycles are easy to be distinguished. The electrocardiogram is a biological signal generated at the beginning of a cardiac cycle. The starting point corresponding to a P wave and the end points corresponding to a QRS wave and a T wave represent breaking points of the cardiac cycle. The pulse wave is a circulatory biological signal easily obtained, from which it is easy to recognize the cardiac cycle. The start point of the waveform and a DN (dicrotic notch) represent breaking points of the cardiac cycle.

When monitoring a plurality of biological signals with the cardiac cycle as a reference, it has been conventional to temporarily stop the sweeping of biological signal waveforms displayed on the monitor screen and manually move the cursor to a particular position of, e.g., an electrocardiogram.

In the case of studying a plurality of biological signals recorded on a recording sheet, two waveforms have been compared with each other either by using the graduation of the recording sheet or by drawing a line by drawing at a timing corresponding to a particular wave position in, e.g., an electrocardiogram.

Thus, in the case of monitoring simultaneously a plurality of biological signals displayed on a monitor screen such as a CRT, comparison of other biological signals with, e.g., an electrocardiogram as a reference is difficult since the waveform is swept, thus making monitoring of the waveform in phase with the cardiac cycle difficult in the conventional art. It is for this reason that the practice of manually moving the cursor to an arbitrary position while stopping the sweeping of the waveform as often as necessary has been performed.

Further, in the case of monitoring biological signals recorded on a recording sheet, the points in time at which the significant waveforms of the biological signals are generated are different from one another. Since a graduation provided on the recording sheet keeps regular intervals, the graduation makes their monitoring in phase with the cardiac cycle difficult. It is for this reason that the practice of drawing a line on the time axis, matching a reference point of the cardiac cycle using a ruler, has been required.

These operations are not only time-consuming, but also not practical in that such operations often must be performed on all heartbeats.

SUMMARY OF THE INVENTION

The invention has been proposed to overcome these problems encountered by the conventional art. Accordingly, an object of the invention is to provide an apparatus for measuring biological signals, which is capable of displaying marker lines on a time axis in synchronism with a particular position of a reference wave so that, if an electrocardiogram is selected as the reference wave, a plurality of other biological signals can be monitored in comparison with the electrocardiogram.

To achieve the above object, the invention is applied to an apparatus for measuring biological signals including an input means for simultaneously receiving and amplifying a plurality of biological signal waveforms; a memory means for storing the plurality of biological signal waveforms input through the input means; a marker line synchronizing position setting means for determining a marker position by setting an arbitrary position of at least a single biological signal waveform that serves as a reference signal selected from the plurality of biological signal waveforms stored in the memory means; a marker line generating means for generating a marker line at the position set by the marker line synchronizing position setting means; and a display unit for not only displaying the plurality of biological signal waveforms stored in the memory means but also displaying the marker line generated by the marker line generating means so as to intersect the time axis of the plurality of biological signal waveforms orthogonally.

According to the present invention, a marker line can be output by the marker line generating means at a position corresponding to some point of the reference cycle of a reference biological signal waveform. Therefore, the position at which the user desires to output the marker line is set by the marker line synchronizing position setting means, whereby the marker line, synchronized with a particular point in the reference biological signal waveform can be displayed so as to be superposed on a plurality of biological signal waveforms based on the output from the marker line generating means.

Further, according to another embodiment of the invention, a composite signal, in which a marker line is superposed upon the position set by the marker line synchronizing position setting means, can be generated by a central processing unit that constitutes part of the marker line generating means. And by receiving the composite signal at the display unit, a marker line synchronized with the particular point of the reference biological signal waveform can similarly be output so as to be superposed on a plurality of biological signal waveforms by the display unit.

BRIEF DESCRIPTION OF THE DRAWINGS

FIG. 4 is a flowchart showing a procedure for outputting a marker line by converting the wave point detecting position to a waveform displaying memory address;

DETAILED DESCRIPTION OF THE PREFERRED EMBODIMENTS

Embodiments of the invention will be described in detail with reference to the drawings. An apparatus for measuring biological signals, which is an embodiment of the invention, is shown in a block diagram in FIG. 1.

This embodiment is designed to measure a plurality of circulatory biological signals and uses an electrocardiogram as a reference waveform to represent a cardiac cycle.

Figure 1:
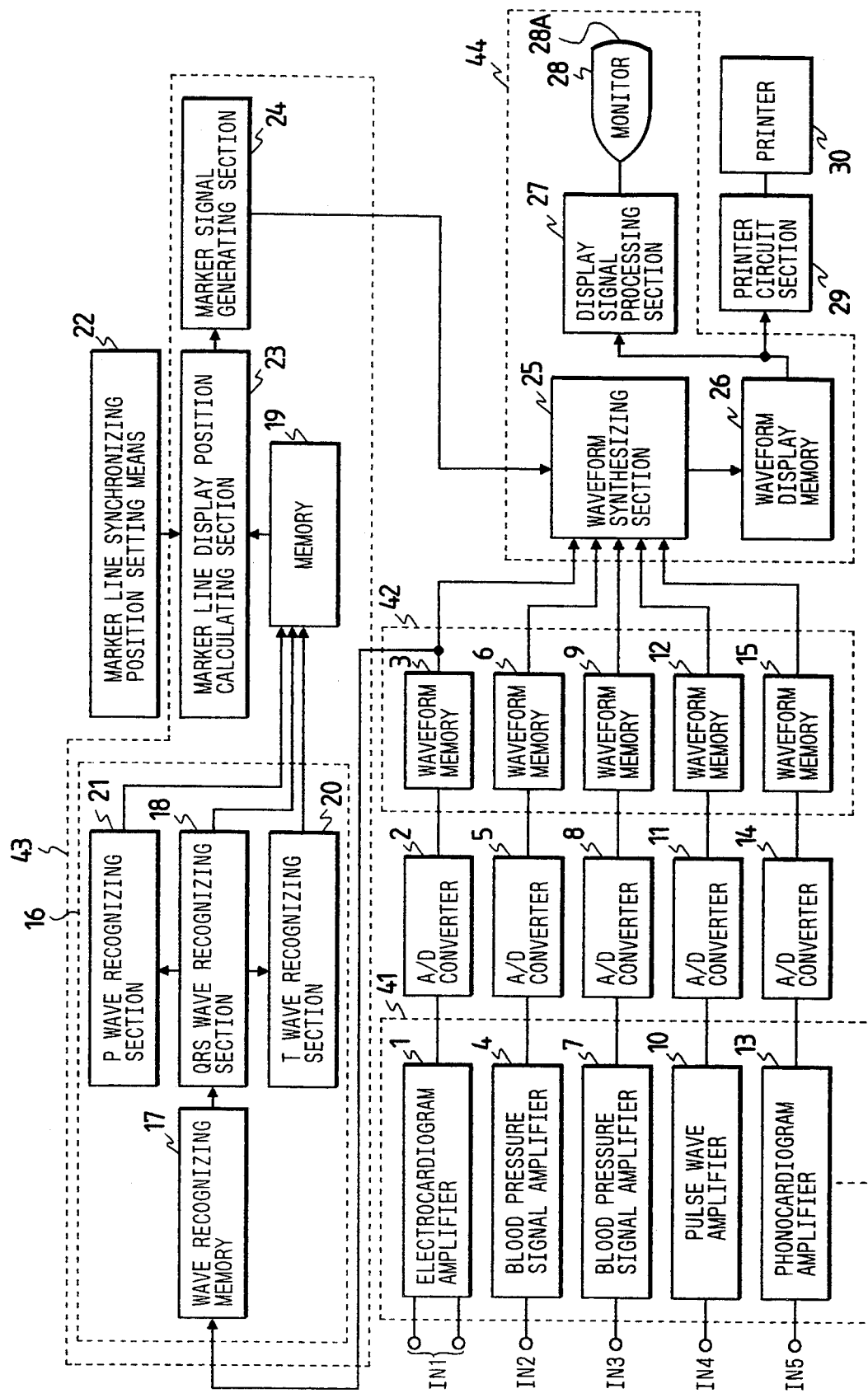
FIG. 1 is a block diagram showing an apparatus for measuring biological signals, according to a first embodiment of the invention.

In FIG. 1, an electrocardiogram signal is led out from a plurality of electrodes attached to a subject (not shown). This electrocardiogram signal is fed to an electrocardiogram amplifier 1 from input terminals IN1 for amplification and then converted to a digital signal at an analog-to-digital converter (hereinafter referred to as "A/D converter") 2. The electrocardiogram signal converted to the digital signal is then stored in a waveform memory 3.

An aortic blood pressure signal and a right ventricular blood pressure signal that are, e.g., obtained in a cardiac catheter examination are supplied to input terminals IN2 and IN3 of blood pressure signal amplifiers 4 and 7, converted at A/D converters 5 and 8, and then stored in waveform memories 6 and 9, respectively.

A pulse wave signal obtained from a transducer attached to the subject is fed to a pulse wave amplifier 10 from an input terminal IN4 to be amplified by an amplifier 10, converted to a digital signal at an A/D converter 11, and stored in a waveform memory 12.

A phonocardiographic signal is led out from a microphone attached to the subject. The phonocardiogram signal is applied to a phonocardiogram amplifier 13 from an input terminal IN5 for amplification, converted to a digital signal at an A/D converter 14, and then stored in a waveform memory 15. The electrocardiogram amplifier 1, the blood pressure signal amplifiers 4, 7, the pulse wave amplifier 10, and the phonocardiogram amplifier 13 constitute an input means 41, which is designed to receive and amplify a plurality of biological signal waves simultaneously. The waveform memories 3, 6, 9, 12, and 15 constitute a memory means 42, which is designed to store the plurality of biological signal waveforms.

Figure 2:
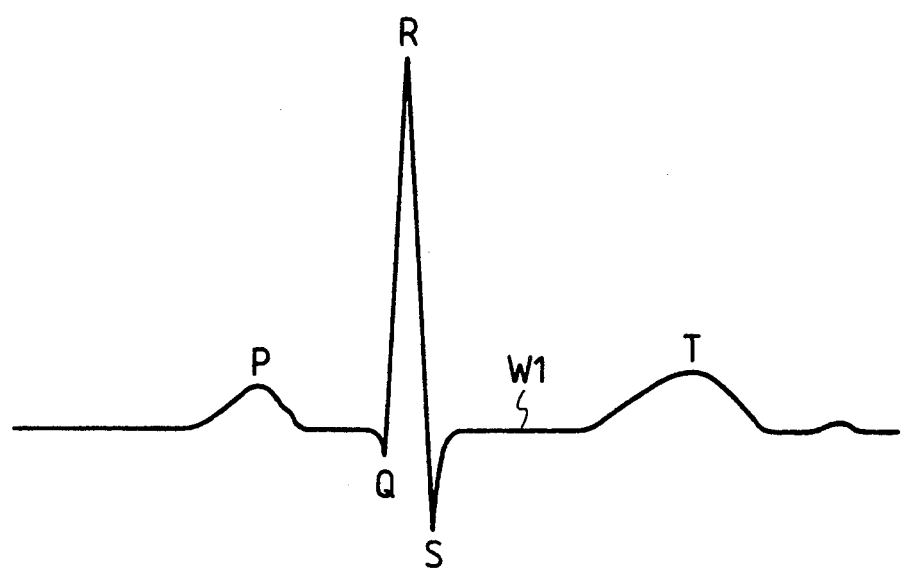
FIG. 2 is a waveform relating to an ordinary electrocardiogram.

The electrocardiogram signal stored in the waveform memory 3 is read by a wave recognizing section 16. As shown by an electrocardiogram W1 in FIG. 2, the wave recognizing section 16 recognizes a P wave corresponding to an excitation period of an atrium, a QRS wave corresponding to a systolic period, and a T wave corresponding to a diastolic period.

Figure 3:
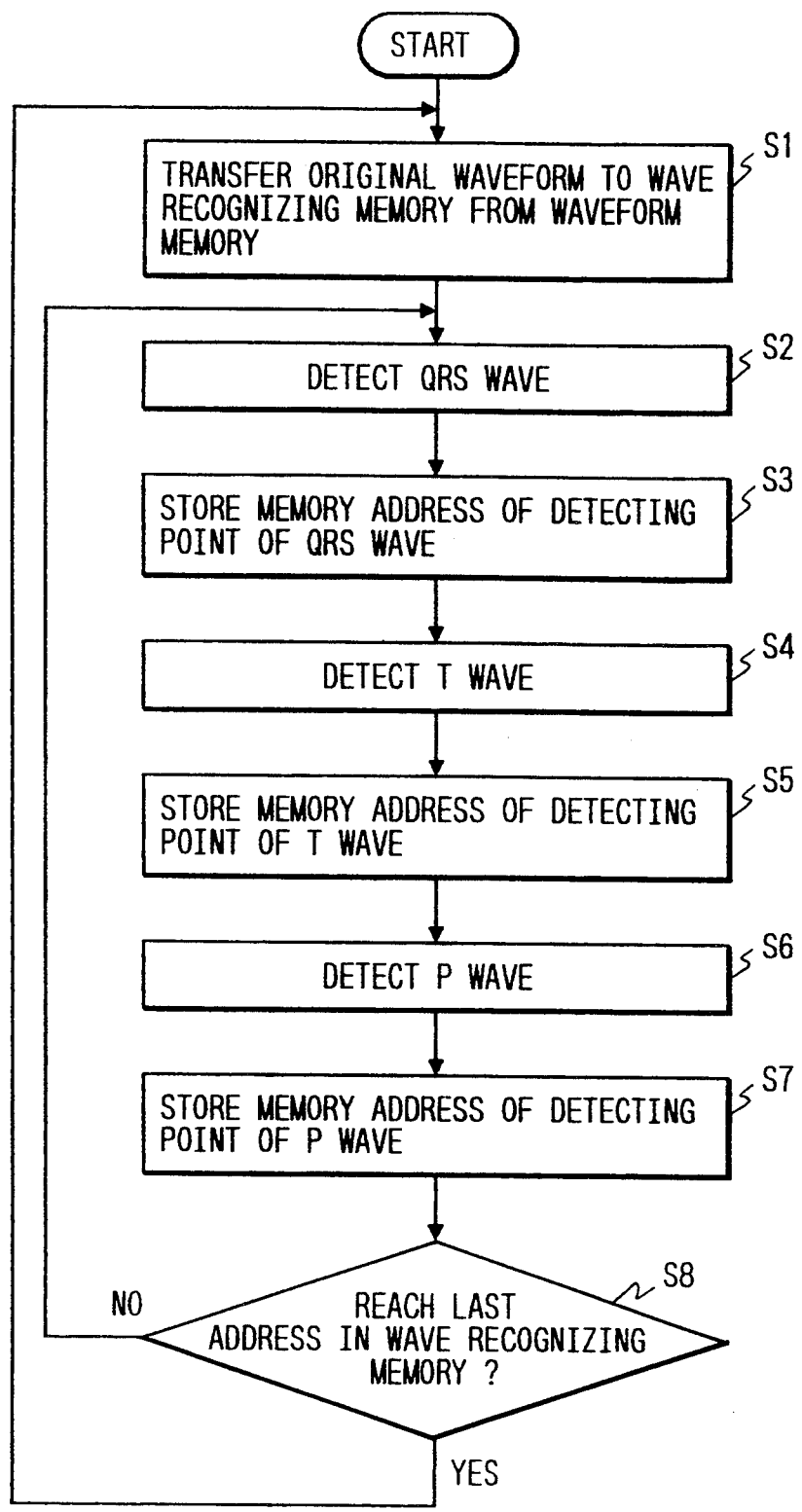
FIG. 3 is a flowchart showing a procedure for recognizing the position for detecting each significant wave point in the electrocardiogram.

A wave recognizing procedure followed by the wave recognizing section 16 will be described with reference to a flowchart shown in FIG. 3. An electrocardiogram W1, which is an original waveform, is transferred to a wave recognizing memory 17 from the waveform memory 3 (Step S1). The electrocardiogram W1 is read from the wave recognizing memory 17 and then applied to a QRS wave recognizing section 18 to detect a QRS wave (Step S2). Conventional methods are employed to detect the QRS wave. After the QRS wave has been detected, data, which is a memory address in the wave recognizing memory 17 corresponding to the detecting onset point of the QRS wave, is stored in a memory 19 (Step S3).

The end point of a T wave that comes after the QRS wave is then detected by a T wave recognizing section 20 based on the data that is the detecting point of the detected QRS wave. The data that is a memory address of the detecting point of the T wave end point is stored in the memory 19 (Steps S4 and S5). Then, a P wave that precedes the QRS wave is detected by a P wave recognizing section 21 based on the detecting point data of the detected QRS wave, and data that is a memory address of the detecting point of the P wave is stored in the memory 19 (Steps S6 and S7).

The processing from Steps S2 to S7 is repeated until the wave recognizing memory 17 reaches the last address thereof. Upon judgment in Step S8 that the last address in the wave recognizing memory 17 has been reached, the electrocardiogram W1, which is the original waveform, is read from the waveform memory 3 again, sent to the wave recognizing memory 17, and subjected to the same processing repetitively.

In the meantime, a marker line synchronizing position setting means 22 can set a position at which a marker line is to be displayed in synchronism with the electrocardiogram W1, the position being on the time axis of the electrocardiogram W1. The marker line synchronizing position setting means 22 can not only select the P, the QRS, or the T wave as a marker line display position, but also set the marker line display position at any arbitrary position shifted horizontally on the time axis from the selected wave position by using a correcting value. For example, the marker line display position can be set as "the QRS wave±a correcting value".

Upon setting of the marker line display position in Step S9 shown in FIG. 4, a setting signal is output from the marker line synchronizing position setting means 22 and sent to a marker line display position calculating section 23. If the marker line is to be displayed in synchronism with the P wave, the display position calculating section 23 reads the memory address of the detecting point of the P wave from the memory 19 and, if a correcting value is involved, converts the address in the memory 19 to an address in a waveform display memory 26 considering the correcting value (Steps S10, S11, and S16). If the marker line is to be displayed in synchronism with the QRS wave, the memory address of the detecting point of the QRS wave is read from the memory 19, and this memory address is converted to data that is a memory address corresponding to the waveform display memory 26 and if a correcting value is involved, this address is converted to an address in the waveform display memory 26 considering the correcting value. (Steps S12, S13 and S16). Further, if the marker line is to be displayed in synchronism with the T wave, the memory address of the detecting point of the T wave is read from the memory 19 and, if a correcting value is involved, this address is converted to an address in the waveform display memory 26 considering the correcting value (Steps S14 to S16). If the address in the wave recognizing memory 17 corresponds to the address in the waveform display memory 26 one to one, the display memory address can be calculated by converting only the correcting value.

An output signal from the marker line display position calculating section 23 is sent to a marker signal generating section 24, at which a marker signal required to display a marker line in the form of a thin or broken bright line is generated. The marker signal generated at the marker signal generating section 24 is sent to a waveform synthesizing section 25. Here, the wave recognizing section 16, the memory 19, the marker line display position calculating section 23, and the marker signal generating section 24 constitute a marker line generating means 43. The marker line generating means 43 is designed to generate a marker line at a position set by the marker line synchronizing position setting means 22.

The waveform synthesizing section 25 receives the electrocardiogram signals, the two blood pressure signals, the pulse wave signal, and the phonocardiogram signal read from the waveform memories 3, 6, 9, 12, 15, and synthesizes these biological signals with the marker signal (Step S17).

A signal synthesizing the biological signals with the marker signal output from the waveform synthesizing section 25 is stored in the waveform display memory 26, sequentially read from the waveform display memory 26, and sent to a display signal processing section 27, where the signal is converted to a display signal that can be displayed on a monitor 28.

Figure 5:
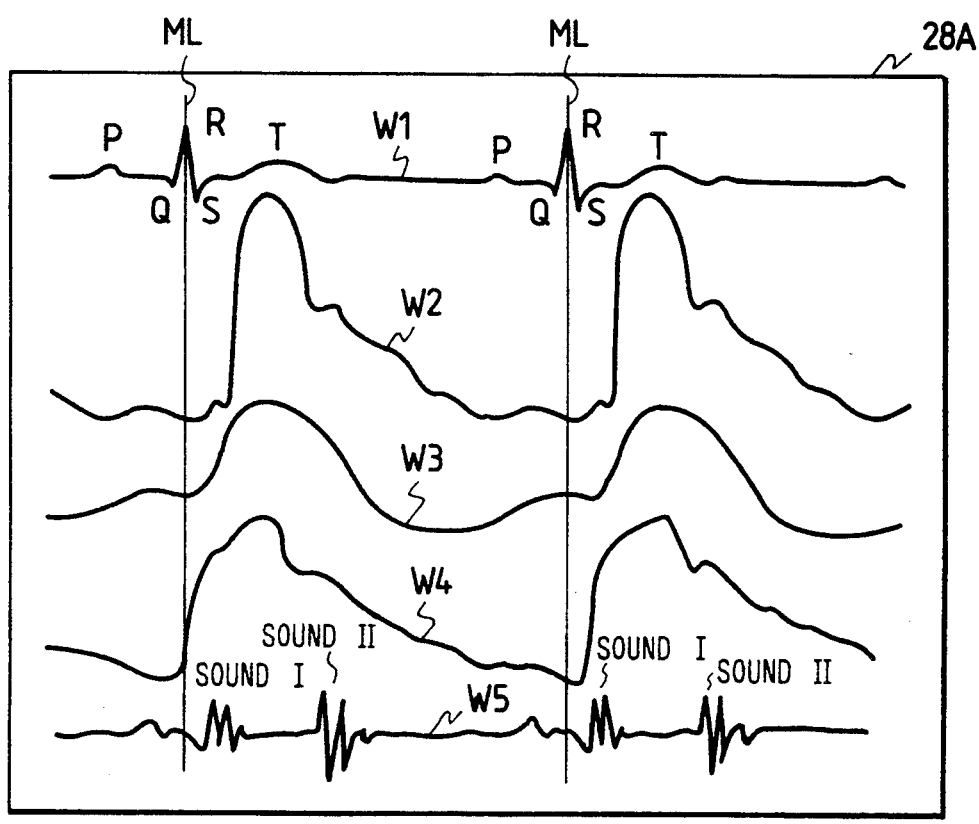
FIG. 5 is a diagram showing waveforms and marker lines displayed on a monitor screen, the waveforms including a plurality of biological signal waveforms and the marker lines being generated in synchronism with, e.g., a significant point of the electrocardiogram.

Accordingly, as shown in FIG. 5, not only a plurality of biological signals including an electrocardiogram W1, an aortic blood pressure wave W2, a right ventricular pressure wave W3, a pulse wave W4, and a phonocardiogram W5 are displayed as continuous waveforms, but also, together therewith, marker lines ML that are synchronized with the positions on the time axis of, e.g., the QRS wave of the electrocardiogram W1 can be displayed on a monitor screen 28A (Step S18). The display of the marker lines allows a plurality of biological signals to be monitored in synchronism with the cardiac cycle of, e.g., the QRS wave of the electrocardiogram W1. Further, a more detailed analysis of biological signal waveforms is possible by correcting the display position of the marker line ML while inputting a correcting value.

When the signal outputted from the waveform display memory 26 is sent to a printer circuit section 29 that constitutes a recording section and processed, marker lines ML synchronized with, e.g., the QRS wave of the electrocardiogram W1 can be depicted so as to be superposed on a plurality of biological signal waveforms to be recorded on a recording sheet by a printer 30, like the waveforms displayed on the monitor screen 28A.

Here, the waveform synthesizing section 25, the waveform display memory 26, the display signal processing section 27, and the monitor 28 constitute a display unit 44. The display unit 44 is designed not only to display a plurality of biological signal waveforms but also to display marker lines generated by the marker line generating means 43 so that the marker lines intersect the time axis of the plurality of biological signal waveforms orthogonally.

Figure 6:
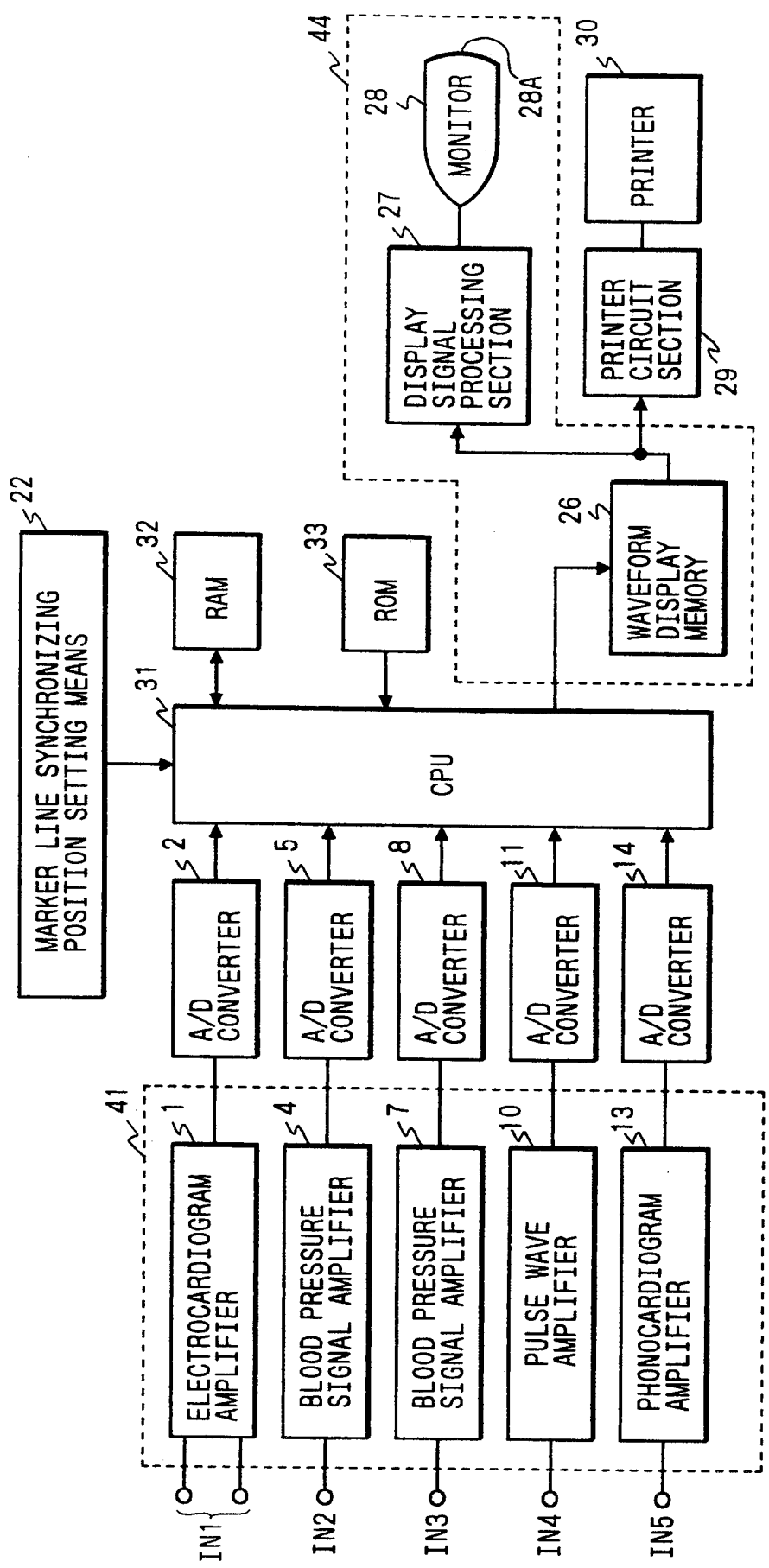
FIG. 6 is a block diagram showing an apparatus for measuring biological signals according to another embodiment of the invention.

An apparatus for measuring biological signals, which is another embodiment of the invention, will be described with reference to FIG. 6. In FIG. 6, the same reference numerals as in FIG. 1 designate the same components. In this embodiment the wave recognizing section 16, the marker line display position calculating section 23, and the marker signal generating section 24, which constitute part of the marker line generating means 43 shown in FIG. 1, are formed of a central processing unit 31 (hereinafter referred to as "CPU 31"). Connected to the CPU 31 are a random access memory 32 (hereinafter referred to as "RAM 32") having a storage area equivalent to the waveform memories 3, 6, 9, 12, 15 constituting the memory means 42, and the memories 17 and 19 constituting part of the marker line generating means 43, as well as a read only memory (hereinafter referred to as "ROM 33") having a program corresponding to a processing procedure of the CPU 31.

The CPU 31 reads the electrocardiogram signal, the two blood pressure signals, the pulse wave signal, and the phonocardiogram signal, which are digital signals output from the A/D converters 2, 5, 8, 11, 14, respectively, and stored in the RAM 32.

The CPU 31 then reads, e.g., the electrocardiogram signal, which is a reference signal, from the RAM 32. The signal is then subjected to a series of processing steps, similar to those of FIG. 3, based on the program stored in the ROM 33. As a result, the respective positions of the P wave, the QRS wave, and the T wave are recognized and respective detected wave position data are stored in the RAM 32.

When the position at which a marker line is to be displayed is set by the marker line synchronizing position setting means 22, the set signal is applied to the CPU 31. Then, the wave position data corresponding to the set position is read from the RAM 32 based on the processing procedure shown in FIG. 4 and is converted to an address in the waveform display memory 26, taking a correcting value at the time of setting into consideration, if applicable.

Upon determination of the marker line output position, a composite signal in which the marker line is superposed on a plurality of biological signal waveforms read from the RAM 32 is generated at the CPU 31 and output to the waveform display memory 26.

Each composite signal sequentially read from the waveform display memory 26 is sent to the display signal processing section 27 to be converted to a signal capable of being displayed on the monitor 28. Accordingly, the marker lines ML synchronized with a particular position of the electrocardiogram W1 can be displayed so as to be superposed on the plurality of biological signal waveforms displayed on the monitor screen 28A as shown in FIG. 5. Further, the marker lines synchronized with the electrocardiogram W1 can be depicted on the plurality of biological signal waveforms to be recorded by the printer 30.

While the above-mentioned two embodiments use the electrocardiogram W1 as a reference waveform of the cardiac cycle, the marker lines ML may be displayed, e.g., with the pulse wave W4 as a reference waveform. If the pulse wave W4 is used, a differential wave or a second order differential wave is generated and a timing at which such wave crosses the wave rising section or the zero level may be used as a time reference. If the pulse wave W4 is used as a reference, not only a time difference with respect to the QRS wave of the electrocardiogram W1 or a time difference with respect to the phonocardiogram W5 can be verified, but also differences between other biological signal waveforms with the pulse wave W4 as the cardiac cycle reference can be studied.

As described in the foregoing pages, the invention is characterized as automatically outputting marker lines in synchronism with a biological signal whose regularity is particularly distinct among a plurality of regularly generated biological signals. That is, the marker lines are generated using such a particular biological signal as a reference. As a result, a comparison between the reference waveform and a plurality of other biological signal waveforms can be made with reference to the marker lines.

Accordingly, when the waveforms of a plurality of circulatory biological signals is to be studied in comparison with, e.g., an electrocardiogram, the present invention permits the user to dispense with not only the cumbersome operation of temporarily stopping the sweeping of a waveform displayed on a monitor screen to move the cursor to the electrocardiogram serving as a reference, but also the cumbersome operation of drawing a guideline that synchronizes with the reference waveform on the recording sheet with a ruler. As such, the present invention provides a distinct advantage over conventional methods.

Further, when a waveform is swept on the monitor screen, it has heretofore been impossible to study a waveform that is synchronized with a reference waveform. However, the invention can display marker lines automatically over a continuous waveform on the monitor screen. As a result, another advantage that one or more additional biological signal waveforms can be monitored in comparison with the reference waveform while detecting a plurality of biological signals from a subject.

Further, since the invention allows the marker line display position to be set arbitrarily so as to synchronize with the reference waveform, the relationship between biological signal waveforms at a desired timing can be studied easily, which is still another advantage.

Therefore, if the apparatus for measuring biological signals of the invention is used, not only can an efficient study of the waveforms of biological signals can be ensured for clinical and/or examination/investigation purposes, but also detailed waveform analysis can be performed, thus tremendously contributing to the improvement of medical care.

What is claimed is:

1. An apparatus for measuring biological signals, comprising:
    an input device receiving and amplifying a plurality of biological signal waveforms simultaneously and outputting amplified signals;
    a memory device, coupled to said input device, said memory device receiving and storing said amplified signals;
    a waveform recognition processor coupled with said memory device and designed to locate at least one predetermined feature of at least one of said biological signal waveforms;
    a marker line synchronizing position setting device, coupled to said waveform recognition processor, said marker line synchronizing position setting device setting a marker position based on a selection input selecting a position relative to said predetermined feature of said at least one biological signal waveform, said at least one biological signal waveform corresponding to a reference signal;
    a marker line signal generating device, coupled to said marker line synchronizing position setting device, said marker line signal generating device receiving said marker position and generating a marker line signal corresponding to said marker position set by said marker line synchronizing position setting device; and
    a display device, coupled to said marker line signal generating device, said display device receiving said amplified signals and said marker line signal, and displaying waveform outputs corresponding to said plurality of biological signal waveforms, and displaying a marker line corresponding to said marker line signal generated by said marker line generating device, whereby said marker line orthogonally intersects a time axis of said plurality of biological signal waveforms.

2. An apparatus for measuring biological signals as claimed in claim 1, wherein said reference signal is an electrocardiographical signal.

3. An apparatus for measuring biological signals as claimed in claim 2, wherein said predetermined feature is at least one of a P wave, a QRS wave or a T wave.

4. A method for displaying a plurality of biological signals, said method comprising the steps of:
    reading waveforms indicative of said biological signals into a memory;
    setting a marker line display position for a marker line, by synchronizing said marker line with one of said biological signals;
    automatically locating at least one predetermined feature of at least one of said waveforms by forming a detecting point;
    reading a memory address of said detecting point;
    converting said memory address into a display address in a waveform display memory;
    generating a marker signal from said marker line display position;
    composing a display of said biological signals and said marker line based on said waveforms, said display address and said marker signal; and
    continuously displaying said display such that said marker line is displayed relative to a time axis of at least one of said biological signals.

5. A method as claimed in claim 4, wherein said biological signals read in said reading step comprises an electrocardiogram.

6. A method as claimed in claim 4, wherein said at least one predetermined feature located in said locating step is one of a P-wave, a QRS-wave, or a T-wave in an electrocardiogram waveform.

7. A method as claimed in claim 4, wherein said at least one predetermined feature located in said locating step is a point in one of said waveforms.

8. A method as claimed in claim 4, wherein said at least one predetermined feature located in said locating step is a pattern in one of said waveforms.

9. A method as claimed in claim 4, wherein said converting step comprises
receiving a correction value; and
determining said display address based on said memory address and said correction value.

10. An apparatus for measuring biological signals, comprising:
an input means for receiving and amplifying a plurality of biological signal waveforms;
a memory means for storing said plurality of amplified biological signal waveforms input through said input means;
a recognizing means for detecting at least one predetermined feature of at least one of said amplified biological signal waveforms and outputting a detected feature signal;
a marker line synchronizing position setting means for setting a marker position based on said detected feature signal;
a marker line generating means for generating a marker line at said marker position set by said marker line synchronizing position setting means; and
a display means for displaying said plurality of biological signal waveforms and displaying said marker line generated by said marker line generating means, whereby said marker line orthogonally intersects a time axis of said plurality of biological signal waveforms.

11. An apparatus for displaying biological signals, comprising:
a signal input designed to receive and digitize a plurality of contemporaneous biological signal waveforms, and to output digitized waveform signals;
a selection input which receives and processes at least one marker line position selection and outputs a setting signal;
a memory, coupled with said signal input, which stores the digitized waveform signals;
a waveform recognition processor coupled with said memory and designed to locate at least one predetermined feature of the biological signal waveforms by processing the digitized waveform signals and outputting at least one feature output;
a marker line position processor, coupled to said waveform recognition processor and said selection input, which receives the at least one feature output, receives the setting signal and generates marker line data based on the at least one feature output and the setting signal;
a display unit, coupled with said memory and said marker line position processor, which generates and displays a composite signal and marker data based on the digitized waveform signals and the marker line data.

12. An apparatus according to claim 11, wherein said memory comprises a random access memory.

13. An apparatus according to claim 11, wherein said signal input comprises an electrocardiogram amplifier.

14. An apparatus according to claim 11, wherein said signal input comprises at least one blood pressure amplifier.

15. An apparatus according to claim 11, wherein said signal input comprises a pulse wave amplifier.

16. An apparatus according to claim 11, wherein said signal input comprises a phonocardiogram amplifier.

17. An apparatus according to claim 11, wherein said waveform recognition processor is designed to locate at least one of a P-wave, a QRS-wave or a T-wave in an electrocardiogram signal waveform.

18. An apparatus according to claim 11, wherein said waveform recognition processor is designed to locate a point in the biological signal waveforms.

19. An apparatus according to claim 11, wherein said waveform recognition processor is designed to locate a pattern in the biological signal waveforms.

20. An apparatus according to claim 11, wherein said selection input is designed to further receive and process at least one correction value.

21. An apparatus according to claim 11, wherein said display unit comprises a video monitor.

22. An apparatus according to claim 11, wherein said display unit comprises a printer.

23. An apparatus according to claim 11, wherein said waveform recognition processor and said marker line position processor comprise a central processing unit and a read-only memory.

* * * * *

UNITED STATES PATENT AND TRADEMARK OFFICE
CERTIFICATE OF CORRECTION

PATENT NO.   : 5,392,780
DATED        : February 28, 1995
INVENTOR(S)  : Yoshio OGINO et al.

It is certified that error(s) appears in the above-identified patent and that said Letters Patent is hereby corrected as shown below:

<u>ON THE TITLE PAGE</u> item [75], delete "Kideki Ito" and insert --Hideki Ito--.

Signed and Sealed this

Fourth Day of July, 1995

Attest:

BRUCE LEHMAN

Attesting Officer     *Commissioner of Patents and Trademarks*